United States Patent
Konda et al.

[11] Patent Number: 5,495,333
[45] Date of Patent: Feb. 27, 1996

[54] METHOD AND APPARATUS OF DETECTING IMPURITIES IN FLUID

[75] Inventors: Akio Konda; Hiroyuki Konaka; Makoto Yamashita, all of Tokyo; Norio Yasuoka, Hyogo; Shigeru Kato, Hyogo; Toshio Kometani, Hyogo, all of Japan

[73] Assignee: Sumitomo Electric Industries, Ltd., Osaka, Japan

[21] Appl. No.: 186,020

[22] Filed: Jan. 25, 1994

Related U.S. Application Data

[63] Continuation-in-part of Ser. No. 95,208, Jul. 23, 1993, abandoned.

[30] Foreign Application Priority Data

Jul. 24, 1992 [JP] Japan .................................. 4-218230
Jul. 12, 1993 [JP] Japan .................................. 5-195459

[51] Int. Cl.$^6$ ................................................. G01N 21/00
[52] U.S. Cl. .......................... 356/339; 356/343; 250/574
[58] Field of Search .................................... 356/335–343, 356/244, 246, 440–442; 250/574, 222.2

[56] References Cited

U.S. PATENT DOCUMENTS

| | | | |
|---|---|---|---|
| 2,775,159 | 12/1956 | Frommer | 356/339 |
| 4,212,539 | 7/1980 | Berber et al. | 356/336 |
| 4,329,052 | 5/1982 | Colombo et al. | 356/335 |
| 4,858,085 | 8/1989 | Von Kohorn . | |
| 4,876,458 | 10/1989 | Takeda et al. | 356/339 |
| 5,041,733 | 8/1991 | Noguchi et al. . | |
| 5,175,596 | 12/1992 | Dick et al. | 356/339 |

FOREIGN PATENT DOCUMENTS

| | | | |
|---|---|---|---|
| 0446692 | 9/1991 | European Pat. Off. . | |
| 3832901 | 4/1989 | Germany . | |
| 8500426 | 1/1985 | WIPO | 356/339 |
| 91/09297 | 6/1991 | WIPO . | |
| 93/07471 | 4/1993 | WIPO . | |

OTHER PUBLICATIONS

IBM Technical Disclosure Bulletin, vol. 28, No. 1, Jun. 1985, pp. 331–332.
Patent Abstracts of Japan, vol. 12, No. 8 (P–654) (2855) Jan. 12, 1988.

*Primary Examiner*—Hoa Q. Pham
*Attorney, Agent, or Firm*—Wenderoth, Lind & Ponack

[57] ABSTRACT

There is provided a method and apparatus of detecting minute impurities in the entire body of a fluid. Part of the passage through which the fluid flows is constituted by a transparent member. Light is emitted in a direction substantially parallel to the longitudinal axis of this part of the fluid passage so as to envelop the same. Light scattered by impurities in the fluid is observed from a direction substantially perpendicular to the direction of the passage to detect any minute impurities in the fluid. The method and apparatus is well-suited for use in systems which extrude molten resin in the formation of plastic products used in an electrical environment in order to detect impurities in the resin which could adversely affect the performance of the products.

18 Claims, 6 Drawing Sheets

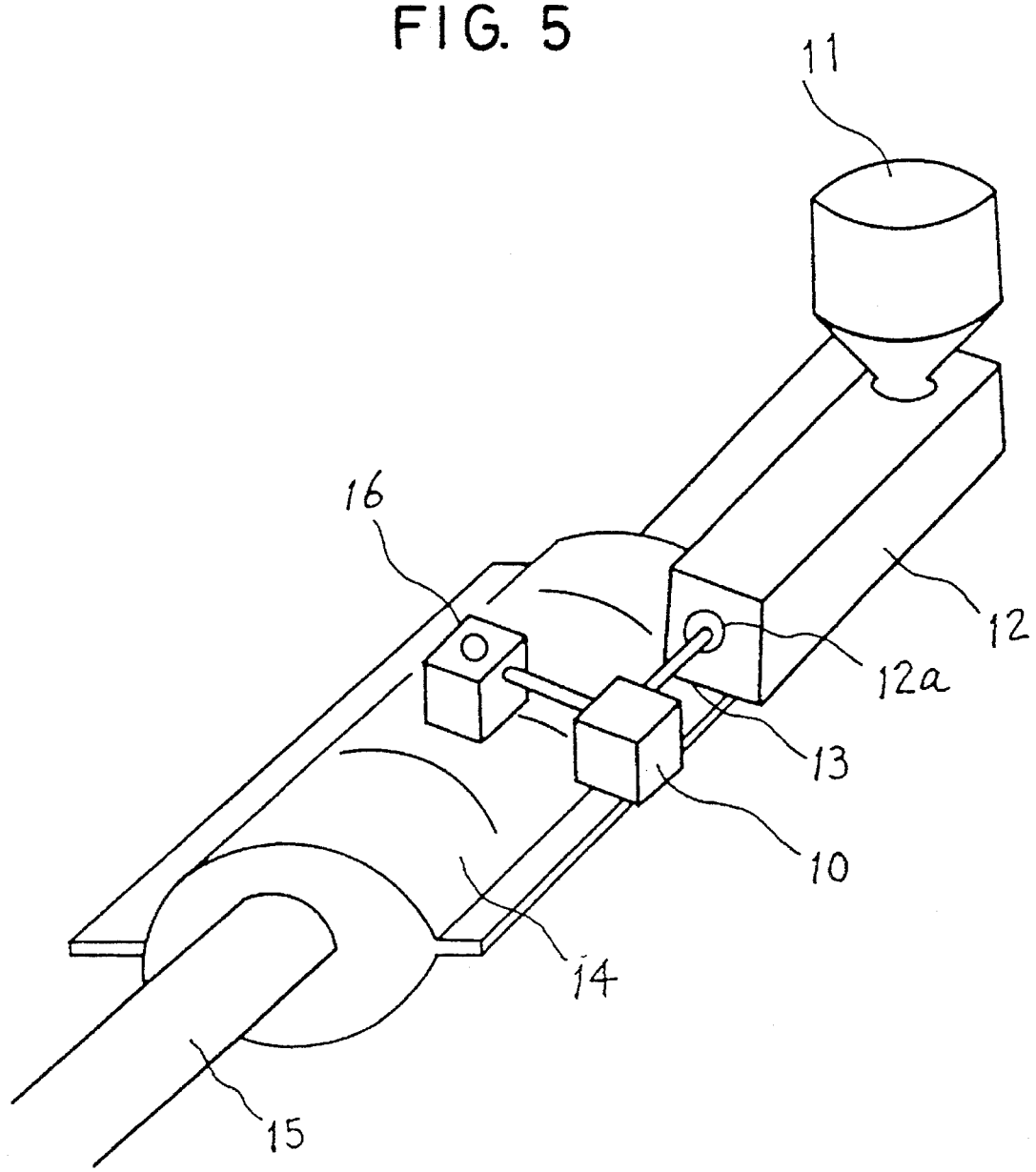

METHOD AND APPARATUS OF DETECTING IMPURITIES IN FLUID

This is a continuation-in-part of U.S. Ser. No. 08/095,208, filed Jul. 23, 1993, now abandoned.

BACKGROUND OF THE INVENTION

The present invention relates to a method and apparatus of detecting any minute impurities contained in a mass of fluid such as a resin flowing in a molten state or a liquid flowing while at normal, high or low temperatures.

If minute impurities are contained, e.g. in a resin used to form an extrusion-molded joint (EMJ) for a high voltage cross-linked polyethylene (XLPE) insulated cable, they may cause electrical troubles. Thus, it is necessary to detect the existence of any impurities in the resin poured into a mold to form an EMJ.

In conventional methods of detecting impurities in a resin, a predetermined amount of resin is sampled continuously and the sampled resin is extruded into a sheet 0.1–0.5 mm thick. The sheet thus formed is inspected by a laser beam transmission or reflecting method to find any impurities (particles of foreign matter of a size larger than 30–40 microns). However, only a sampled-out portion of the fluid is inspected by these methods and not the entire body of fluid.

In a method of detecting impurities in a liquid medicine, a portion of the liquid is bypassed and guided into a passageway 51 made of transparent glass as shown in FIG. 4A. A laser beam is directed at a constricted portion 51a of the glass passageway from a laser 52 toward a light collector 53. When the laser beam impinges impurities in the fluid, the beam will be scattered. Part of the light scattered sideways is received by a light receptor 54 such as a photomultiplier, which produces photoelectric signals. The magnitudes of these signals are compared with those of reference signals to estimate the size and quantity of the impurities flowing in the fluid. This method, too, is a sampling method and does not result in an inspection of the entire body of fluid for impurities.

SUMMARY OF THE INVENTION

An object of the present invention is to provide a method and apparatus for detecting impurities in a fluid, such as molten resin, by observing substantially the entirety of the fluid in order to obtain an accurate depiction of the impurities in the fluid.

The method and apparatus of detecting minute impurities in a fluid is characterized in that part of a fluid passage is defined by a transparent member and a light beam is emitted substantially along the longitudinal axis of the fluid passage so as to envelop the passage, and in that light scattered by impurities in the fluid is observed from a direction substantially perpendicular to the direction in which the fluid flows in the fluid passage, whereby minute impurities in the fluid may be discriminated.

Extensive considerations were given to techniques for efficiently detecting minute impurities in the entire body of fluid to be inspected.

A glass pipe having an inner diameter of 25 mm and a length of 300 mm was prepared. A liquid having substantially the same optical characteristics (light transmittance, refraction factor, etc.) as a crosslinked polyethylene (XLPE) compound in a molten state was sealed in this glass pipe. Foreign matters (such as glass balls and metallic fibers) of several microns to several millimeters in diameter were mixed with the liquid. Light was directed (projected) at the pipe and scattered light beams were observed by a CCD camera. The glass pipe and the CCD camera were moved at a speed of 10 mm/sec relative to each other.

It was found out that by emitting light from one end of the glass pipe with the CCD camera set at one side of the pipe, the amount and shape of the impurities could be accurately determined from the light scattered sideways from the pipe. It was also found out that by setting the angle between the optical axis of the projected light and the direction in which the CCD camera is trained at 90 degrees, 100% of the impurities were detected. At angles other than 90 degrees, the detection rate was poorer due to, for example, total reflection or failure to pick up the scattered beams of light completely.

With the method and apparatus according to the present invention, minute particles of foreign matter in the entire body of fluid can be detected easily and reliably. Detection accuracy is high compared with the conventional sampling method.

Thus, the present invention can be advantageously applied to systems which extrude cable insulation or produce extrusion-molded joints or in a production line of liquid products such as liquid medicines and foodstuffs.

BRIEF DESCRIPTION OF THE DRAWINGS

Other features and objects of the present invention will become apparent from the following description made with reference to the accompanying drawings, in which:

FIG. 5 is a schematic diagram of a system for producing an EMJ of a high voltage cable and employing the detecting method and apparatus according to the present invention.

DETAILED DESCRIPTION OF THE PREFERRED EMBODIMENTS

Figure 1A:
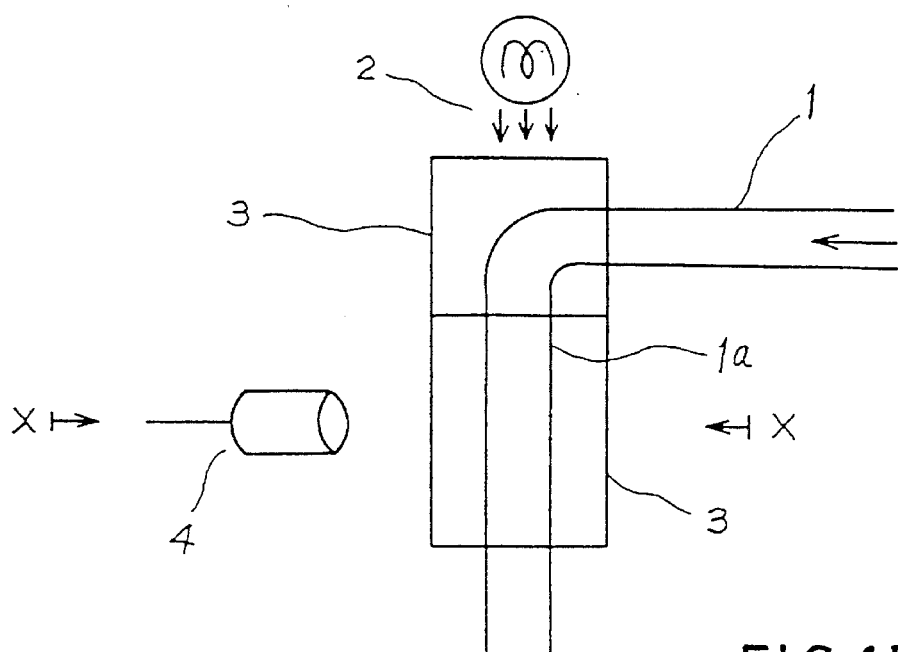
FIG. 1A is a schematic diagram of one embodiment of an apparatus for detecting impurities according to the present invention.
Figure 1B:
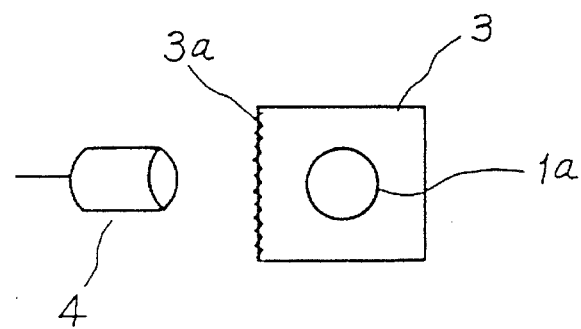
FIG. 1B is a sectional view taken along line 1B—1B of FIG. 1A.

Referring to FIG. 1A, a passage 1 through which a high-temperature molten resin is fed from an extruder to a mold is bent at a right angle so that the passage extends parallel to a beam of light 2 projected from a light source such as a halogen lamp or the like. A portion 1a of the passage 1 is formed by a transparent member 3 such as a crystal glass member and serves as an observation zone. As shown in FIG. 1B, the outer periphery of the transparent member 3 is square and the portion 1a of the passage has a circular cross section.

The light 2, produced by a halogen lamp or the like, is collected by a suitable means and transmitted toward the transparent member 3 in a direction substantially along the axis of the portion 1a of the passage 1 so as to envelop this portion of the passage 1. A CCD camera 4 is disposed substantially perpendicular to the optical axis (and thus to the axis of the portion 1a of the passage) and its focal distance and focal depth are suitably adjusted so that the camera 4 will receive light scattered sideways by impurities in the fluid.

The observation zone is shielded entirely by being housed in a box in order to prevent the CCD camera 4 from picking up any external light. Also, in order to prevent the molten resin from being cooled by contact with the glass, the temperature in the box is kept at 120°–130° C. by an electric heater provided in the box. Further, if necessary, the outer surface of the transparent member may be provided with a total reflection-proof coating 3a at the observation zone. Also, a plurality of CCD cameras 4 may be used. The passage may have a sectional shape other than a circle. For example, it may have an oval or similar cross section.

With this arrangement, a molten resin can be fed through the passage 1 at a constant speed without the possibility of being cooled.

A molten resin containing metallic, fibrous particles or other kinds of impurities of several microns to several millimeters in diameter was extruded into the passage 1. The projected light was scattered upon hitting the impurities and the scattered light was observed by the CCD camera. The images of impurities were successfully received by the CCD camera. Of the images of the impurities (in the scattered light) received by the CCD camera, those exceeding a predetermined level were discriminated and memorized by triggering. The sizes of the impurities resulting from image analysis by a computer were fairly true to the actual sizes of the impurities.

However, it was also found out that when the scattered light was observed by only a single CCD camera 4, i.e. from only one side of the square transparent member 3 in the manner described above, impurities flowing near the inner wall surface of the transparent member 3 were difficult to detect because they were shadowed and no scattered light was produced. This results in poor detection accuracy because all the impurities are not picked up by the camera.

Figure 2A:
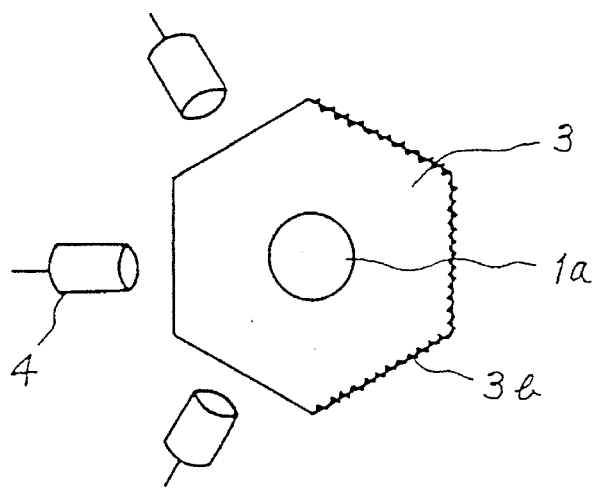
FIG. 2A is a sectional view of another embodiment of an apparatus for detecting impurities according to the present invention.

In order to solve this problem, in the embodiment shown in FIG. 2A, a transparent member 3 having a hexagonal cross section and three CCD cameras 4 were used as shown in the figure. The three sides 3b diametrically opposite to the sides directly facing the CCD cameras 4 were blackened or subjected to light absorption treatment.

With this arrangement, the entire area of the portion 1a of the passage 1 was within the combined field of view of the CCD cameras 4. All of the scattered light and hence, 100% of the images of the impurities were received by the CCD cameras 4. If the flow velocity of the fluid is too high for the CCD cameras to pick up all of the scattered light, a shutter mechanism may be provided on each CCD camera to observe the scattered light more vividly.

Figure 2B:
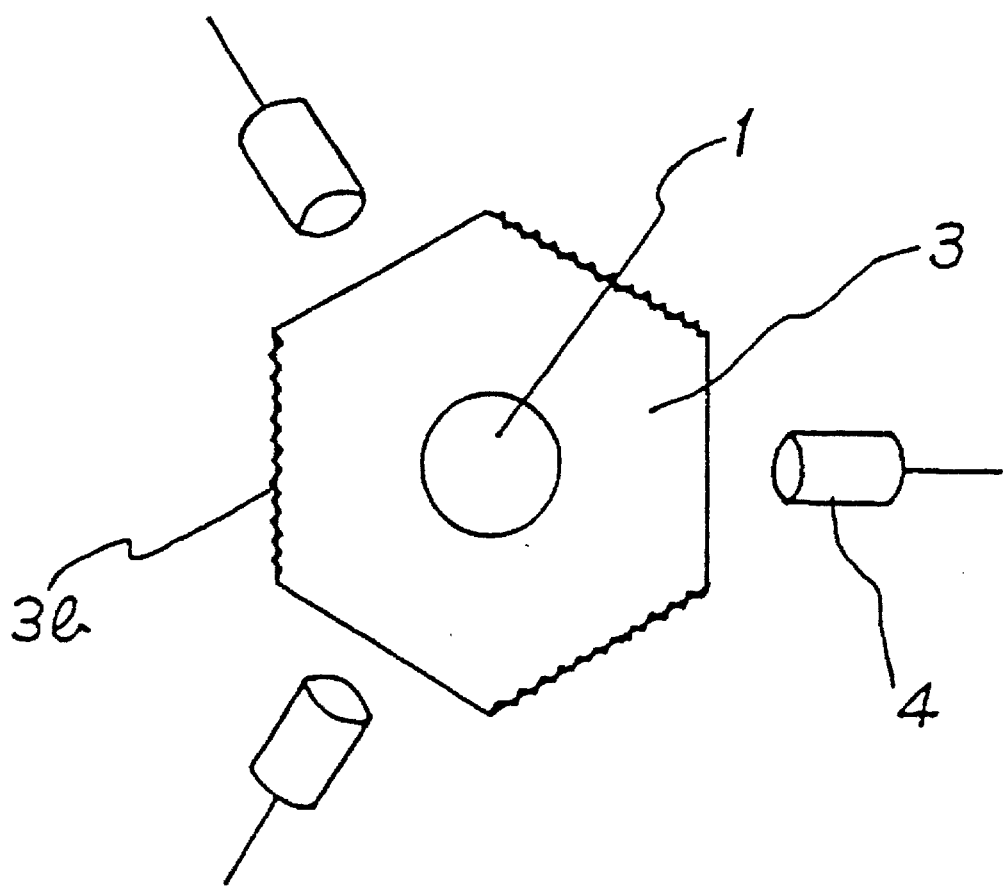
FIG. 2B is a sectional view of another embodiment of an apparatus for detecting impurities according to the present invention.

Alternatively, as shown in FIG. 2B, the CCD cameras 4 can be arranged adjacent every other side of the transparent member 3. The sides 3b opposite those sides adjacent the CCD cameras 4 are also blackened or treated to absorb and not reflect light.

The incident light may 1) have such a wavelength that it exhibits a high transmittance in a liquid, 2) have such a wavelength that it exhibits a high reflectance from minute impurities, 3) be a visible light having a wide wavelength band, which is introduced through a light-collecting system such as a lens, 4) be a laser beam produced by a continuous oscillation laser capable of oscillating wavelengths having a high transmittance in a fluid, or 5) in the case where the flow velocity of the fluid is high, be converted by means of a high-speed shutter into light pulses synchronized with the image processing system in order that scattered beams of light will be observed more vividly.

Figure 3:
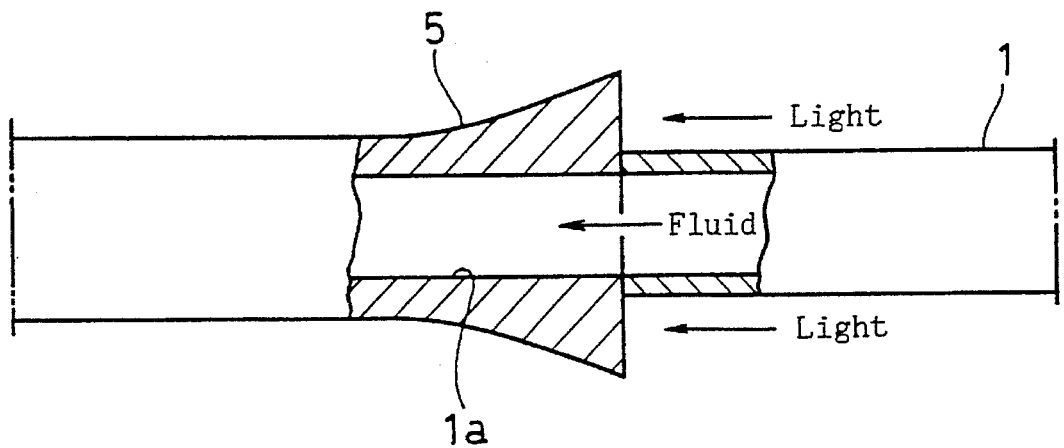
FIG. 3 is a view showing another way of projecting light according to the method of the present invention.
Figure 4A:
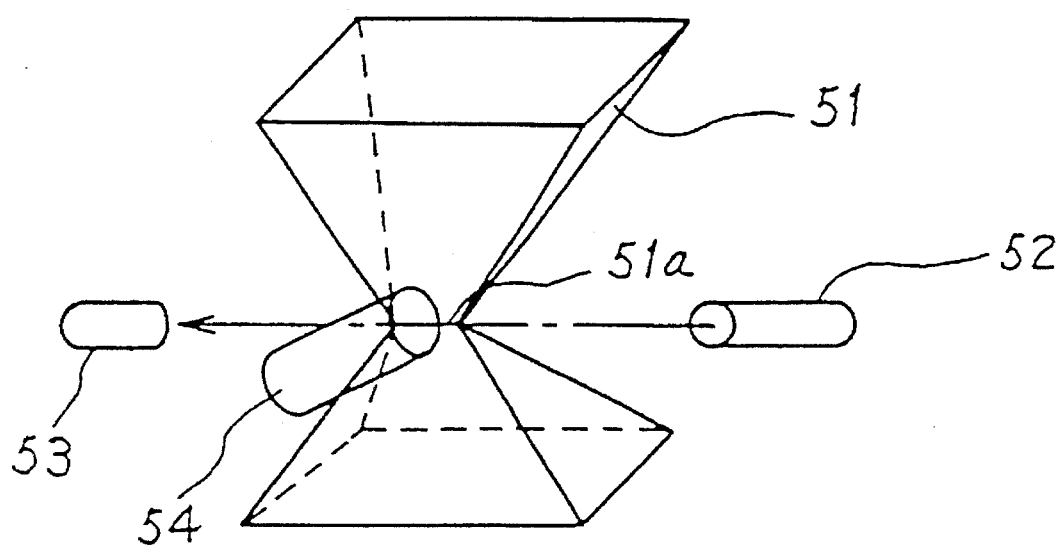
FIG. 4A is a schematic diagram illustrating a conventional method of detecting impurities in a fluid.
Figure 4B:
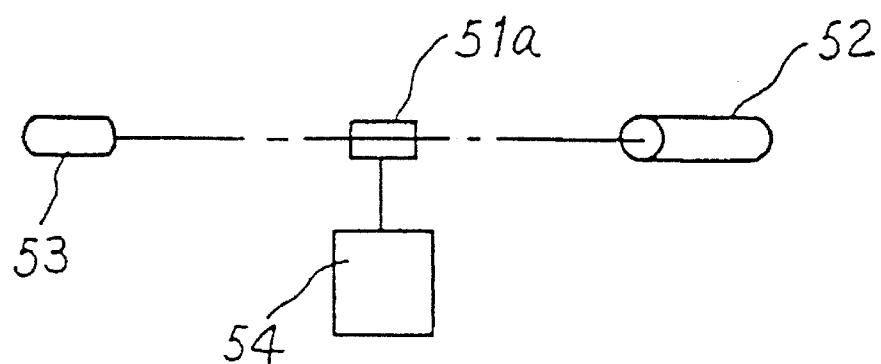
FIG. 4B is a circuit diagram of the apparatus shown in FIG. 4A.

In order for the light to be emitted in a direction substantially parallel to the passage, the light may be passed through a coaxial glass pipe 5 as shown in FIG. 3. Although FIG. 3 shows the light being emitted in the same direction of fluid flow, the light may alternatively be emitted in a direction opposite to the direction of fluid flow.

The incident light may be emitted from a ring-shaped (annular) lamp, employing an optical fiber, directly at the transparent member. In this case, it is not necessary to provide a bend at a right angle in the passage 1 upstream of the observation zone. This improves the freedom of design and flexibility in constructing the system. The light is reflected from the outer surface of the glass pipe or otherwise disperses to within the passage 1a.

When a high-temperature or low-temperature fluid is to be inspected, the materials of the glass member and the metal member in the observation zone should be selected taking their coefficient of thermal expansion into consideration. Further, it is necessary to provide a suitable leak-preventive means (seal) on the joint.

In FIG. 5, numeral 10 designates a box in which the detecting apparatus shown in FIG. 1 is housed. A resin in the form of pellets in a tank 11 is fed to an extruder 12 where the resin is heated and melted. A fine filter 12a is disposed at the exit of the extruder. The high-temperature molten resin extruded from the extruder 12 is fed through a fluid passageway 13 to the transparent member of the detecting apparatus housed in box 10 and then to a mold 14 containing a portion of a cable 15. Any impurities contained in the molten resin are detected by the detecting apparatus in the detector box 10 and are expelled from the system by a discharge valve unit 16.

Figure 6:
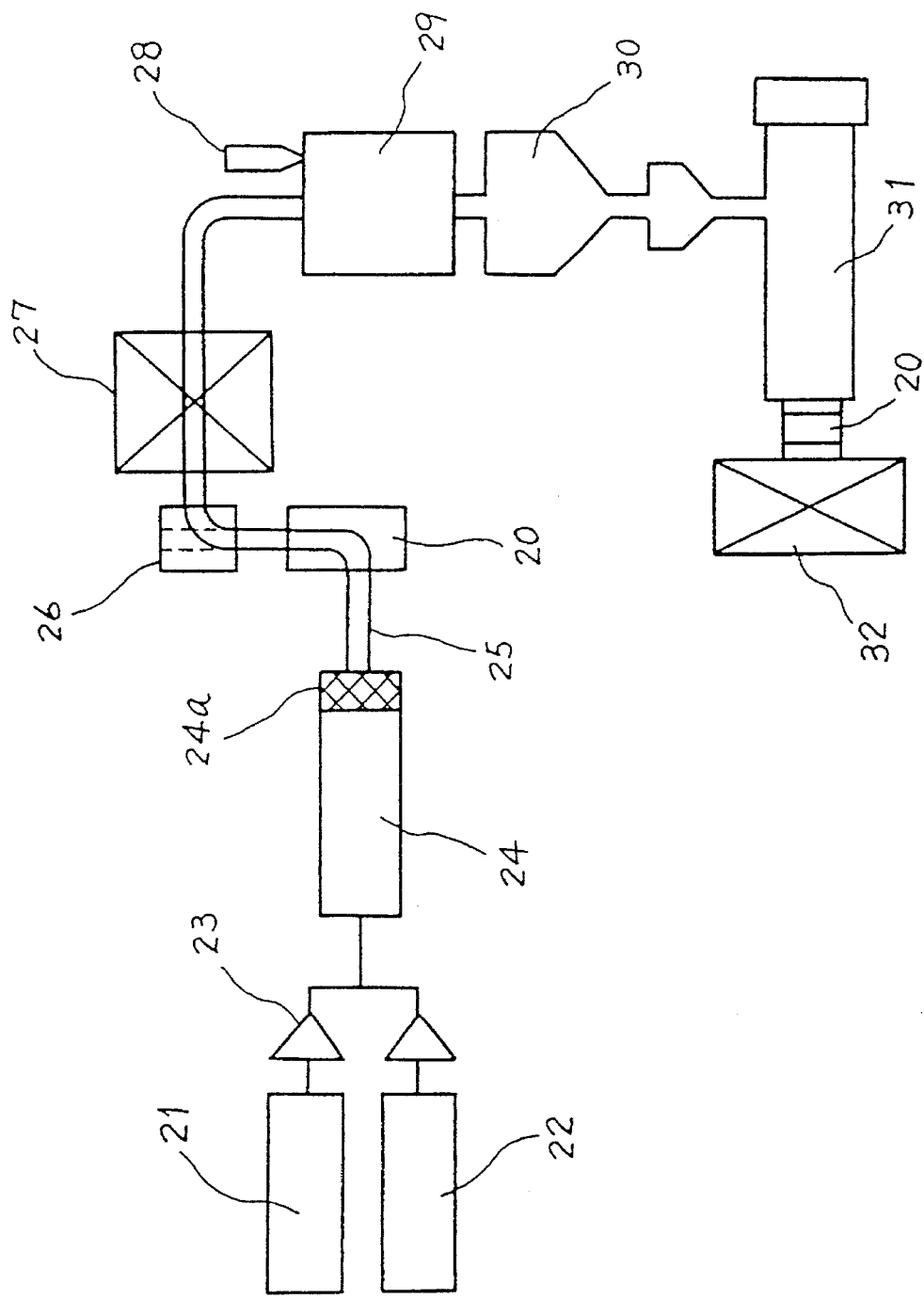
FIG. 6 is a block diagram of a system for extruding cable insulation and employing the detecting method and apparatus according to the present invention.

As shown in FIG. 6, resin pellets in a resin storage section 21 and an antioxidant 22 are weighed at 23, mixed and melted at a section 24 of the system and fed through a fine filter 24a to a fluid passageway 25. Reference numeral 20 designates a detecting apparatus according to the present invention, which serves to detect impurities contained in the molten resin. The resin is fed from the apparatus or unit 20 through a pelletizer 27 to a portion 29 of the system at which the resin is impregnated with a crosslinking agent.

If impurities are detected by the detecting apparatus 20, the resin is discharged out of the passageway through a discharging portion 26 having a changeover valve. The resin, having been impregnated with a crosslinking agent, is stored temporarily in a hopper 30 and supplied at a predetermined rate to an extruder 31. The resin is then extruded by a cross head 32 to form cable insulation or the like.

Since it is not necessary to provide a bend at a right angle in the fluid passage just before the detecting apparatus, the apparatus 20 can be disposed between the extruder 31 and the cross head (or forming portion) 32. With this arrangement, impurities can be detected just before the forming step.

Although the present invention has been described above in connection with preferred embodiments thereof, various changes and modifications will become apparent to those of ordinary skill in the art. For instance, although the transparent member shown in FIGS. 2A and 2B has a hexagonal outer periphery, the periphery may be of other polygonal shapes having an even number of sides. In this case, optical detectors such as CCD cameras will be provided to face only one of each pair of diametrically opposite sides of the transparent member. All such changes and modifications are seen to be within the true spirit and scope of the invention as defined by the appended claims.

What is claimed is:

1. A method of detecting minute impurities in a fluid, said method comprising:

feeding a fluid, to be inspected for minute impurities, through a passage defined by a transparent member, the passage having a longitudinal axis;

directing an annular beam of light into said transparent member substantially along the longitudinal axis of said passage, whereby light is reflected from impurities in the fluid; and observing the light reflected from the impurities from a direction substantially perpendicular to the longitudinal axis with at least one optical detector to thereby detect the presence of impurities in the fluid.

2. A method as claimed in claim 1, wherein the feeding of fluid comprises feeding fluid to be inspected for impurities through a passage defined by a transparent member having an outer periphery of a polygon shape having an even number of sides, and the observing of the light reflected from the impurities comprises observing the light with respective optical detectors facing only one of each pair of diametrically opposite sides of the transparent member.

3. Apparatus for detecting minute impurities in a fluid, said apparatus comprising:

a transparent member defining a fluid passageway therein through which passage fluid to be inspected for impurities is to flow;

an optical system comprising a light source oriented to direct an annular beam of light into said transparent member substantially along the longitudinal axis of said passage, whereby light will be reflected from impurities in the fluid; and at least one optical detector oriented to receive, from a direction substantially perpendicular to said longitudinal axis, light emitted by said optical system and reflected from impurities in the fluid.

4. Apparatus as claimed in claim 3, wherein said transparent member has an outer periphery of a polygon shape having an even number of sides, and said at least one optical detector comprises optical detectors facing only one of each pair of diametrically opposite sides of said transparent member.

5. Apparatus as claimed in claim 4, wherein the optical detectors face every other side of said transparent member in the circumferential direction thereof.

6. The apparatus of claim 3, wherein said light source comprises an annular lamp.

7. Apparatus as claimed in claim 6, wherein said transparent member has an outer periphery in a polygon shape having an even number of sides, and said at least one optical detector comprises optical detectors facing only one of each pair of diametrically opposite sides of said transparent member.

8. Apparatus as claimed in claim 7, wherein the optical detectors face every other side of said transparent member in the circumferential direction thereof.

9. A system for forming a plastic article, said system comprising: an extruder for extruding resin, a detecting apparatus for detecting impurities in the resin, and a fluid passageway connected to said extruder and said apparatus, said detecting apparatus comprising a transparent member defining a fluid passage therein in-line with said fluid passageway such that resin flowing through said fluid passageway flows through said transparent member, the fluid passage having a longitudinal axis, an optical system comprising a light source oriented to direct an annular beam of light into said transparent member substantially along the longitudinal axis of said passage, whereby light will be reflected from impurities in the resin, and at least one optical detector oriented to receive, from a direction substantially perpendicular to said longitudinal axis, light emitted by said optical system and reflected from impurities in the resin.

10. A system as claimed in claim 9, wherein said fluid passageway has one end connected to an outlet of said extruder, and further comprising a mold connected to the other end of said fluid passageway.

11. A system as claimed in claim 10, and further comprising a discharge valve disposed in said fluid passageway between said detecting apparatus and said mold.

12. A system as claimed in claim 10, and further comprising a resin pellet storage section, and a resin pellet melting section connected to said storage section so as to receive pellets of resin therefrom and melt the pellets, and wherein said fluid passageway is connected between said pellet melting section and said extruder.

13. A system as claimed in claim 12, and further comprising a discharge valve disposed in said fluid passageway between said detecting apparatus and said extruder, whereby molten resin is discharged from the system before reaching said extruder when a predetermined amount of impurities are detected in the resin by said detecting apparatus.

14. The system of claim 9, wherein said light source comprises an annular lamp.

15. A system as claimed in claim 14, wherein said fluid passageway has one end connected to an outlet of said extruder, and further comprising a mold connected to the other end of said fluid passageway.

16. A system as claimed in claim 15, and further comprising a discharge valve disposed in said fluid passageway between said detecting apparatus and said mold, whereby resin extruded from said extruder is discharged from the system before reaching said mold when a predetermined amount of impurities are detected in the resin by said detecting apparatus.

17. A system as claimed in claim 15, and further comprising a resin pellet storage section, and a resin pellet melting section connected to said storage section so as to receive pellets of resin therefrom and melt the pellets, and wherein said fluid passageway is connected between said pellet melting section and said extruder.

18. A system as claimed in claim 17, and further comprising a discharge valve disposed in said fluid passageway between said detecting apparatus and said extruder, whereby molten resin is discharged from the system before reaching said extruder when a predetermined amount of impurities are detected in the resin by said detecting apparatus.

* * * * *